United States Patent [19]
Ishikawa et al.

[11] Patent Number: 5,498,717
[45] Date of Patent: Mar. 12, 1996

[54] 6,7-DIALKOXY-3,4-DIYDROISOQUINOLIN-8-YL COMPOUNDS

[75] Inventors: Kiyofumi Ishikawa; Takashi Hayama, both of Tsukuba, Japan

[73] Assignee: Banyu Pharmaceutical Co., Ltd., Tokyo, Japan

[21] Appl. No.: 288,551

[22] Filed: Aug. 10, 1994

Related U.S. Application Data

[62] Division of Ser. No. 199,691, Feb. 22, 1994, Pat. No. 5,446,164.

[30] Foreign Application Priority Data

Feb. 25, 1993 [JP] Japan ................. 5-060846

[51] Int. Cl.⁶ ................. C07D 217/14; C07D 217/16
[52] U.S. Cl. ................. 546/139; 546/90; 546/147; 546/148; 546/149
[58] Field of Search ................. 546/90, 139, 147, 546/148, 149; 514/291, 307

[56] References Cited

FOREIGN PATENT DOCUMENTS

| | | | |
|---|---|---|---|
| 0028279 | 5/1981 | European Pat. Off. | 546/149 |
| 2368277 | 5/1978 | France | 546/149 |
| WO-8807041 | 9/1988 | WIPO | 546/149 |
| WO90/02119 | 8/1990 | WIPO | 546/149 |

OTHER PUBLICATIONS

Short et al., Tetrahedron, 1973, vol. 29, No. 14, pp. 1931–1939.
Chem. Pharm. Bull., 15, 879, Jun. 1967, Kametani et al "Studies of the Syntheses etc.".
J. Chem. Soc., (C), 715, 1966 Kametani et al. "Studies on the Syntheses of Heterocyclic etc.".
Helv. Chim. Acta, 49, 1757, 1966 Brossi et al "Synthesen in der Isochinolinreihe etc.".
J. Chem. Soc., (C), 1796, 1971 Kametani et al "Studies on the Syntheses of Heterocyclic Compounds etc.".
J. Am. Chem. Soc., 92 (No. 23), 6943–6951 (1970) Kapadia et al "On the Origin of Carbon 1 in etc.".
Monatsh, 43, 477 (1922) Spath "Uber die Anhaloniumalkaloide etc.".
Berichte., 65, 1778 (1932) Spath "Uber die Konstitution von Pellotin etc.".
The Merck Index vol. 11, 682 (1989) "Anhalamine".
J. Am. Chem. Soc., 74, 2864 (1952) Manske "The Alkaloids of Fumariaceous Plants etc.".

*Primary Examiner*—Bernard Dentz
*Assistant Examiner*—Zinna N. Davis
*Attorney, Agent, or Firm*—Nixon & Vanderhye

[57] ABSTRACT

This invention relates to novel 6,7-dialkoxy-3,4-dihydroisoquinolin-8-ols, a process for preparing the 6,7-dialkoxy-3,4-dihydroisoquinolin-8-ols reioselectively and in a high yield utilizing the Bischler-Napieralski reaction, a process for synthesizing the 6,7-dialkoxy-1,2,3,4-tetrahydroisoquinolin-8-ols via the compounds, and use of the 6,7-dialkoxy-3,4-dihydroisoquinolin-8-ols for preparation of the 6,7-dialkoxy-1, 2,3,4-tetrahydroisoquinolin-8-ols.

It is possible according to this invention, to obtain the 6,7-dialkoxy-1,2,3,4-tetrahydroisoquinolin-8-ols, which have hitherto been difficult to synthesize, via the 6,7-dialkoxy-3,4-dihydroisoquinolin-8-ols in a high yield.

1 Claim, No Drawings

6,7-DIALKOXY-3,4-DIYDROISOQUINOLIN-8-YL COMPOUNDS

This a division of application Ser. No. 08/199,691, filed Feb. 22, 1994 now U.S. Pat. No. 5,446,164.

FIELD OF THE INVENTION AND RELATED ART STATEMENT

This invention relates to 6,7-dialkoxy-3,4-dihydroisoquinolin-8-ols useful as intermediate raw materials for synthesis of isoquinolines having a hydroxyl group or a lower alkoxy group at the 8-position of the isoquinoline skeleton, useful as an antitumor effect potentiator for anticancer agent in the pharmaceutical field (see, PCT/JP89/00825, WO 90/02119), a process for preparation thereof and a process for preparation of 6, 7-dialkoxy-1,2,3,4-tetrahydroisoquinolin-8-ols (e.g., dl-corpaverine, anhalamine, etc.) using the compounds.

As an example of processes for preparation of 6,7-dialkoxy-1,2,3,4-tetrahydroisoquinolin-8-ols, a synthetic process by the Bischler-Napieralski reaction is known. In the case of synthesizing, for example, dl-corpaverine using this synthetic process, there is reported a route, as shown in the following Reaction formula A, to obtain such a desired produce by subjecting a 3,4-dihydroisoquinoline obtained as a mixture of regioisomers after cyclization reaction to several steps including separation of the isomers (*Chem. Pharm. Bull.*, 15, 879, 1967).

Reaction formula A:

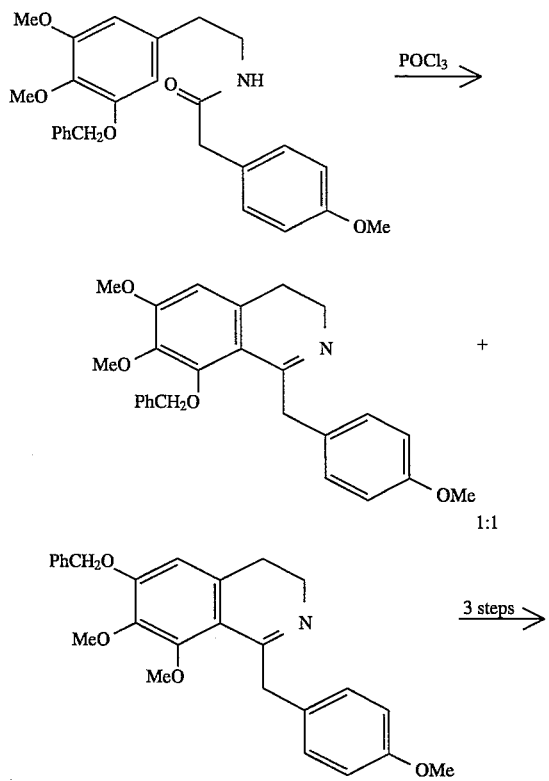

Reaction formula A: -continued

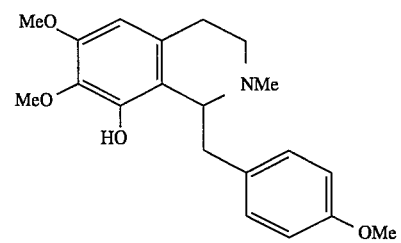

Further as an example of regioselective synthesis, a route using the Pomeranz-Fritsch reaction as shown in the following Reaction formula B is known (*J. Chem. Soc., (C)*, 715, 1966).

Reaction formula B:

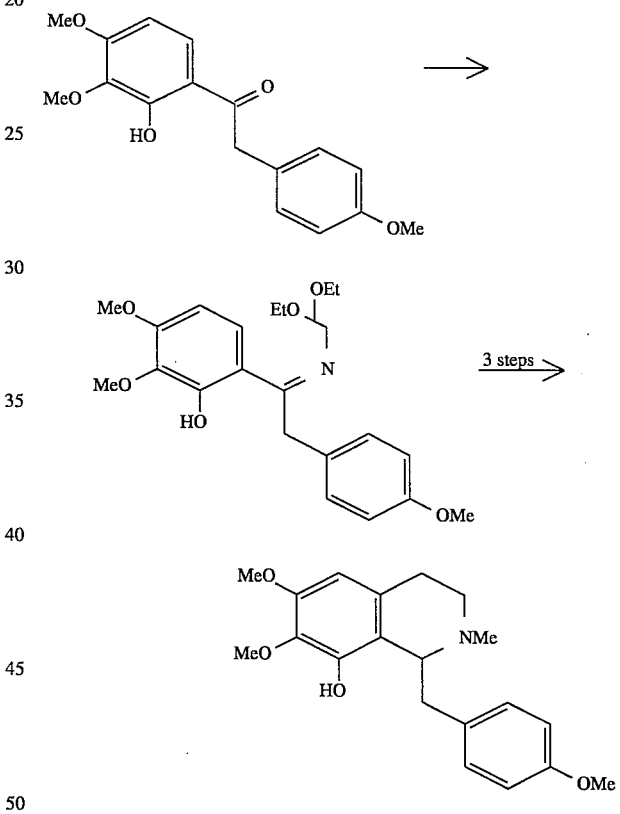

Further, as a process for preparation of a tetrahydroisoquinolin-8-ol having a substituent at the 1-position, a route using the Grignard reaction with 2-methyl-3,4-dihydroisoquinolium bromide as a raw material, as shown in Reaction formula C, is reported (Helv. Chim. Acta, 49, 1757, 1966).

Reaction formula C:

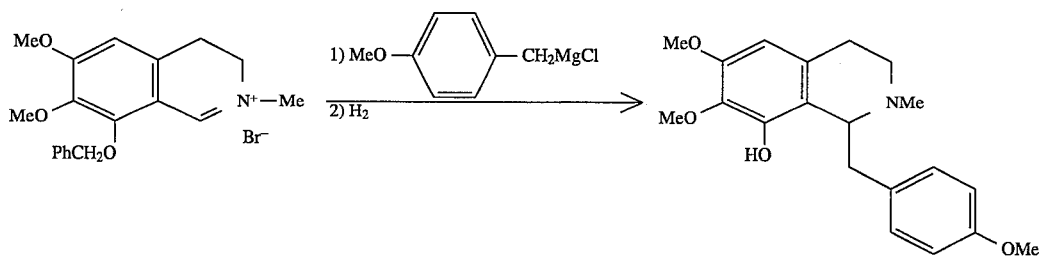

Further, as an example wherein the Bischler-Napieralski reaction was carried out using a phenethylamide derivative having a phenolic hydroxyl group at the 3-position as a raw material to progress a selective cyclization at the ortho position of the phenolic hydroxyl group, it has hitherto been reported that the direction of cyclization was controlled in one direction by introducing a bromine atom at the para position of the phenolic hydroxyl group as a blocking group participating in the cyclization, as shown in Reaction formula D (*J. Chem. Soc. (C)*, 1796, 1971).

Reaction formula D:

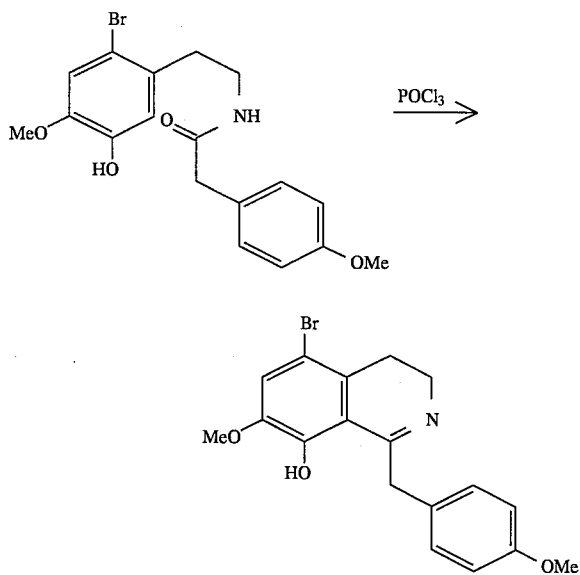

Further, in *J. Am. Chem. Soc.*, 92 (No. 23), 6943–6951 (1970), the following in vitro reactions are carried out using $^*CH_3COCO_2H$ ($^*C = {}^{14}C$) in order to verify a biosynthetic mechanism.

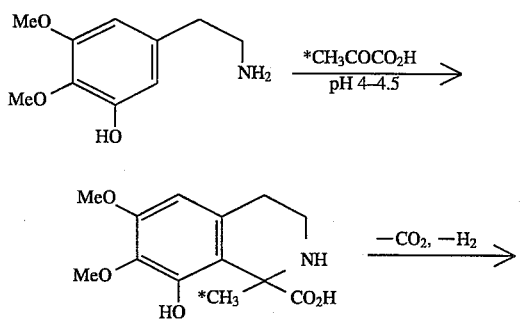

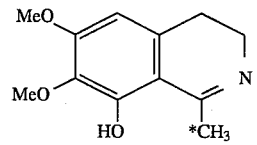

Further in the above literature, an authentic compound for identification of the final product of the above step is synthesized according to the following Reaction formula E.

Reaction formula E:

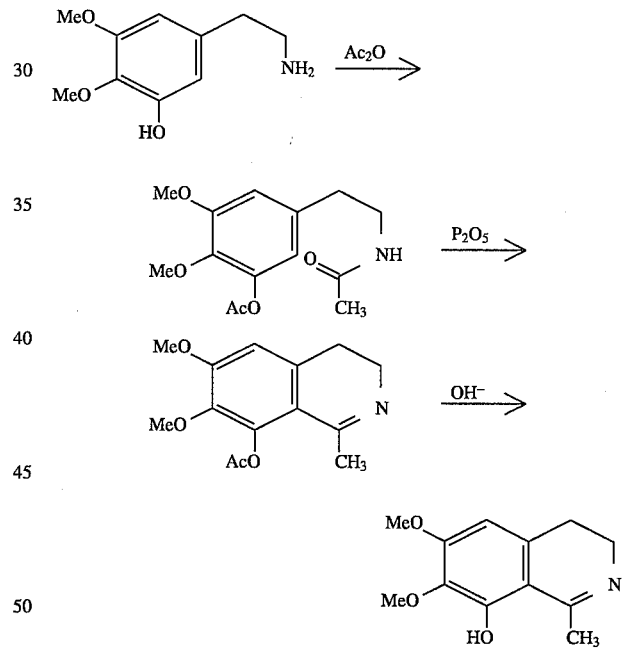

wherein Ac is $CH_3CO-$.

The above steps up to the second step are disclosed in Monatsh, 43, 477 (1922) and Ber., 65, 1778 (1932), and the third step is disclosed in the above *J. Am. Chem. Soc.*, 92 (No. 23), 6943–6951 (1970).

However, a reaction wherein the Bischler-Napieralski reaction is carried out using a phenethylamide derivative having a phenolic hydroxyl group at the 3-position and dialkoxy group at the 4- and 5-positions represented by the formula [II] of this invention is novel and not disclosed in literature, and, moreover, it is not disclosed nor suggested that a 6,7-dialkoxy-3,4-dihydroisoquinolin-8-ol represented by the formula [I] can be obtained in a good yield by cyclizing the derivative selectively at the ortho position of the phenolic hydroxyl group.

In the case of synthesis directed to a 6,7-dialkoxy-1,2 3,4-tetrahydroisoquinolin-8-ol by a known process, the synthetic route using the Bischler-Napieralski reaction gives an unnecessary regioisomer along with the desired one because, as shown in Reaction formula A, there are two cyclization directions and it is impossible to control the cyclization regioselectively to the desired direction, and as a result, the yield of the desired product becomes low and furthermore separation of the isomeric mixture is usually difficult, and thus this process cannot be utilized for large scale synthesis.

Further, the synthetic route using the Pomeranz-Fritsch reaction shown by Reaction formula B has difficulties in raw material synthesis and of a low total yield, and cannot be utilized for large scale synthesis, either.

The process for preparation of a 1-substituted tetrahydroisoquinolin-8-ol shown by Reaction formula C does not fit for large scale synthesis of the desired product, either, because it is not easy to synthesize a raw material in short steps of 2-methyl -3,4-dihydroisoquinolium bromide.

The process to control the direction of cyclization by introducing a bromine atom as a blocking group as shown by Reaction formula D does not fit for large scale synthesis of the desired product, because it is not easy to synthesize a bromo derivative as a raw material and it is necessary to remove the blocking group after the cyclization reaction.

The process for preparation of a 1-substituted tetrahydroisoquinolin-8-ol illustrated in Reaction formula E needs both protection and deprotection steps of the phenolic hydroxyl group with an acetyl group, which limits an application scope of the reaction and becomes a disadvantage for large scale synthesis of the desired product.

Thus, it is difficult, utilizing these conventional processes, to prepare 6,7-dialkoxy-1,2,3,4-tetrahydroisoquinolin-8-ols industrially in a large quantity, and an industrially useful preparation process for this class of compounds is desired.

OBJECT AND SUMMARY OF THE INVENTION

Thus an object of this invention lies in providing a process which makes it possible to prepare 6,7-dialkoxy-1,2,3,4-tetrahydroisoquinolin- 8-ols industrially in a large quantity.

A further object of this invention lies in providing a process for preparing 6,7-dialkoxy-1,2,3,4-tetrahydroisoquinolin-8-ols in a high yield.

A further object of this invention lies in providing a process which makes it possible to prepare 6,7-dialkoxy-1, 2,3,4-tetrahydroisoquinolin-8-ols in relatively short steps.

A further object of this invention lies in providing novel intermediates in the above preparation process.

A further object of this invention lies in providing a process for preparing the above intermediates in a high yield.

A further object of this invention lies in providing a process for preparation of 6,7-dialkoxy-1,2,3,4-tetrahydroisoquinolin-8-ols from the above intermediates.

A further object of this invention lies in providing use of the above intermediates for preparation of 6,7-dialkoxy-1, 2,3,4 -tetrahydroisoquinolin-8-ols.

The present inventors have paid their attention to the point that 6,7-dialkoxy-3,4-dihydroisoquinolin-8-ols are novel compounds whose efficient preparation process has not so far been known; have intensely studied a process for preparing 6,7-dialkoxy-3,4-dihydroisoquinolin-8-ols, which are excellent precursors for preparation of 6,7-dialkoxy-1, 2,3,4-tetrahydroisoquinolin-8-ols in short steps and in a high yield, by subjecting phenethylamide derivatives as a raw material to regioselective cyclization in the Bischler-Napieralski reaction; have found reaction conditions for controlling the direction of cyclization in the Bischler-Napieralski reaction directly using phenethylamide derivatives with an unprotected phenolic hydroxyl group; and have thus completed this invention.

Thus, this invention relates to a compound represented by the following formula or a salt thereof

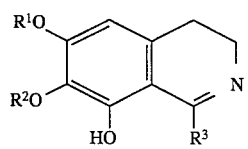

wherein $R^1$ and $R^2$ independently denote a lower alkyl or benzyl group, or are combined together to form a methylene group; and $R^3$ denotes a hydrogen atom, or lower alkyl group, denotes a benzyl group wherein 1 to 3, optional hydrogen atom(s) on the benzene ring may be replaced by any substituent(s) selected from the group consisting of a lower alkoxy group, a benzyloxy group, a halogen atom, a nitro group and a lower alkoxycarbonylmethyl group, denotes a phenethyl group wherein 1 to 3, optional hydrogen atom(s) on the benzene ring may be replaced by a lower alkoxy or benzyloxy group, or denotes a heteroarylmethyl or heteroarylethyl group, provided that when $R^3$ is a methyl group, $R^1$ and $R^2$ are not simultaneously methyl groups; a process for preparation of a compound represented by the following formula or a salt thereof

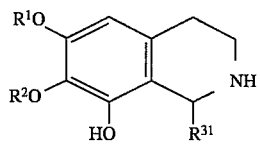

wherein $R^1$ and $R^2$ independently denote a lower alkyl or benzyl group, or are combined together to form a methylene group; and $R^{31}$ denotes a hydrogen atom, or a lower alkyl group, denotes a benzyl group wherein 1 to 3, optional hydrogen atom(s) on the benzene ring may be replaced by any substituent(s) selected from the group consisting of a lower alkoxy group, a benzyloxy group, a halogen atom, a nitro group and a lower alkoxycarbonylmethyl group, denotes a phenethyl group wherein 1 to 3, optional hydrogen atom(s) on the benzene ring may be replaced by a lower alkoxy or benzyloxy group, or denotes a heteroarylmethyl or heteroarylethyl group, which comprises cyclizing a compound represented by the formula

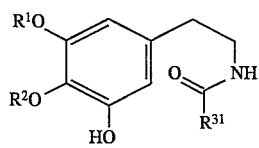

wherein $R^1$, $R^2$ and $R^{31}$ are as defined above, in the presence of a phosphoric acid halide, regioselectively at the ortho position of the phenolic hydroxyl group to form a compound represented by the following formula or a salt thereof

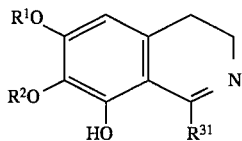

wherein $R^1$, $R^2$ and $R^{31}$ are as defined above, and then reducing the compound or salt;

a process for preparation of a compound represented by the following formula or a salt thereof

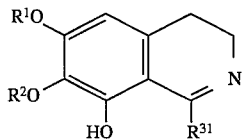

wherein $R^1$ and $R^2$ independently denote a lower alkyl or benzyl group, or are combined together to form a methylene group; and $R^{31}$ denotes a hydrogen atom, or a lower alkyl group, denotes a benzyl group wherein 1to 3, optional hydrogen atom(s) on the benzene ring may be replaced by any substituent(s) selected from the group consisting of a lower alkoxy group, a benzyloxy group, a halogen atom, a nitro group and a lower alkoxycarbonylmethyl group, denotes a phenethyl group wherein 1 to 3, optional hydrogen atom(s) on the benzene ring may be replaced by a lower alkoxy or benzyloxy group, or denotes a heteroarylmethyl or heteroarylethyl group, wherein comprises cyclizing a compound represented by the formula

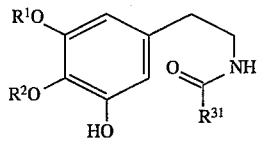

wherein $R^1$, $R^2$ and $R^{31}$ are as defined above, in the presence of a phosphoric acidhalide, regioselectively at the ortho position of the phenolic hydroxyl group;

a process for preparation of a compound represented by the following formula or a salt thereof

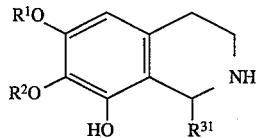

wherein $R^1$ and $R^2$ independently denote a lower alkyl or benzyl group, or are combined together to form a methylene group; and $R^{31}$ denotes a hydrogen atom, or a lower alkyl group, denotes a benzyl group wherein 1 to 3, optional hydrogen atom(s) on the benzene ring may be replaced by any substituent(s) selected from the group consisting of a lower alkoxy group, a benzyloxy group, a halogen atom, a nitro group and a lower alkoxycarbonylmethyl group, denotes a phenethyl group wherein 1 to 3, optional hydrogen atom(s) on the benzene ring may be replaced by a lower alkoxy or benzyloxy group, or denotes a heteroarylmethyl or heteroarylethyl group, which comprises reducing a compound represented by the formula or a salt thereof

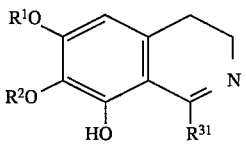

wherein $R^1$, $R^2$ and $R^{31}$ are as defined above; and use of a compound represented by the formula

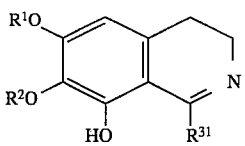

wherein $R^1$ and $R^2$ independently denote a lower alkyl or benzyl group, or are combined together to form a methylene group; and $R^{31}$ denotes a hydrogen atom or a lower alkyl group, denotes a benzyl group wherein 1to 3, optional hydrogen atom(s) on the benzene ring may be replaced by any substituent(s) selected from the group consisting of a lower alkoxy group, a benzyloxy group, a halogen atom, a nitro group and a lower alkoxycarbonylmethyl group, denotes a phenethyl group wherein 1 to 3, optional hydrogen atom(s) on the benzene ring may be replaced by a lower alkoxy or benzyloxy group, or denotes a heteroarylmethyl or heteroarylethyl group, for preparation of a compound represented by the formula

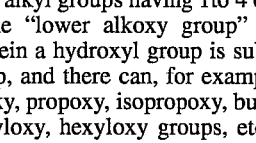

wherein $R^1$, $R^2$ and $R^{31}$ are as defined above, as a useful synthetic intermediate for medicines such as an antitumor effect potentiator.

Now, various terms referred to throughout the specification and included in the range of this invention are defined below and specific examples are also give below.

The term "lower" means, unless otherwise defined, that a group modified by this term has 6 or less carbon atoms. Therefore, the "lower alkyl group" means a straight-chain or branched alkyl group having 1 to 6carbon atoms, and specifically, there can be mentioned methyl, ethyl, propyl, isopropyl, butyl, isobutyl, sec-butyl, tert-butyl, pentyl, isopentyl, neopentyl, tert-pentyl, hexyl groups, etc., and among them alkyl groups having 1to 4 carbon atoms are preferable.

The "lower alkoxy group" means an alkyloxy group wherein a hydroxyl group is substituted by the above alkyl group, and there can, for example, be mentioned methoxy, ethoxy, propoxy, isopropoxy, butoxy, isobutoxy, sec-butoxy, pentyloxy, hexyloxy groups, etc., and among them alkoxy groups having 1 to 4 carbon atoms are preferable, and methoxy, ethoxy and isopropoxy groups, etc. are particularly preferable.

The "lower alkoxycarbonylmethyl group" means an alkoxycarbonylmethyl group wherein the hydroxyl group of a hydroxycarbonylmethyl group is substituted by the above lower alkyl group, and there can, for example, be mentioned methoxy-carbonylmethyl, ethoxycarbonylmethyl, propoxycarbonylmethyl, isopropoxycarbonylmethyl, butoxycarbonylmethyl groups, etc., and among them alkoxycarbonylmethyl groups having 3 to 6 carbon atoms are preferable, and a methoxycarbonylmethyl group is particularly preferable.

As the "halogen atom", there can be mentioned a fluorine atom, a chlorine atom, a bromine atom or an iodine atom.

The "heteroarylmethyl group" means a methyl group substituted by a heteroaryl group. The heteroaryl group means an aromatic heterocyclic group, and means preferably a 5- or 6-membered aromatic heterocyclic group which contains, in the case of the 5-membered ring, 1 to 4 nitrogen atoms, one sulfur or oxygen atom, or 1 or 2 nitrogen atoms and one sulfur or oxygen atom, and contains, in the case of the 6-membered ring, 1 or 2 nitrogen atoms, to which one benzene ring may be condensed, and wherein the heterocyclic ring and/or the benzene ring condensed thereto may have thereon one or two substituents, preferably one substituent selected from a methyl group, a methoxy group, a chlorine atom and a bromine atom. As such heteroaryl groups, there can, for example, be mentioned 2-pyridyl, 3-pyridyl, 4-pyridyl, 4-methyl-2-pyridyl, 4-methoxy-2-pyridyl, 6-methyl-3-pyridyl, 4-methoxy-3-pyridyl, 3-methoxy-4-pyridyl, 2-thienyl, 3-thienyl, 2-pyrrolyl, 3-pyrrolyl, 1-methyl-2-pyrrolyl, 1-methyl-3-pyrrolyl, 2-thiazolyl, 4-thiazolyl, 5-thiazolyl, 4-methyl-2-thiazolyl, 2-methyl-4-thiazolyl, 2-imidazolyl, 4-imidazolyl, 1-methyl-2-imidazolyl, 2-oxazolyl, 4-oxazolyl, 5-oxazolyl, 2-indolyl, 3-indolyl, 5-methyl-3-indolyl, 2-methyl-3-indolyl, 5-methoxy-3-indolyl, 5-bromo-3-indolyl, 2-quinolyl, 3-quinolyl, 4-quinolyl, 3-methyl-4-quinolyl, 1-isoquinolyl, 3-isoquinolyl, 10methyl-4-isoquinolyl, 4-methoxy-1-isoquinolyl groups, etc.

The "heteroarylethyl group" means an ethyl group substituted by the above heteroaryl group.

As the "phosphoric acid halide", there can, for example, be mentioned phosphoryl chloride ($POCl_3$), phosphorus pentachloride, phosphoryl bromide ($POBr_3$), etc.

As preferred lower alkyl groups of $R^1$ and $R^2$, there can, for example, be mentioned methyl, ethyl, propyl, isopropyl groups, and methyl groups are particularly preferable. Although $R^1$ and $R^2$ may be the same or different, it is preferable that they are the same.

As preferred lower alkyl groups of $R^3$, there can, for example, be mentioned methyl, ethyl, propyl, isopropyl, butyl, pentyl, hexyl groups, etc.

As to $R^3$, the kind of substituents in the benzyl group wherein 1 to 3, optional hydrogen atom(s) on the benzene ring may be replaced by any substituent(s) selected from the group consisting of a lower alkoxy group, a benzyloxy group, a halogen atom, a nitro group and a lower alkoxycarbonylmethyl group, may be not only one but two or more, but preferably one or two, and the number of the substituents in total is preferably 1 to 3, particularly preferably 1 or 2. Preferred examples of such optionally substituted benzyl groups are benzyl, 2-methoxybenzyl, 3-methoxybenzyl, 4-methoxybenzyl, 2,3-dimethoxybenzyl, 3,4-dimethoxybenzyl, 2,5-dimethoxybenzyl, 3,5-dimethoxybenzyl, 3,4,5-trimethoxybenzyl, 2-benzyloxybenzyl, 3-benzyloxybenzyl, 4-benzyloxybenzyl, 3-benzyloxy-4-methoxybenzyl, 4-benzyloxy-3-methoxybenzyl, 4-ethoxybenzyl, 4-propoxybenzyl, 2-chlorobenzyl, 3-chlorobenzyl, 4-chlorobenzyl, 2-bromobenzyl, 3-bromobenzyl, 4-bromobenzyl, 2-fluorobenzyl, 3-fluorobenzyl, 4-fluorobenzyl, 4-benzyloxy-3-bromobenzyl, 3-bromo-4-methoxybenzyl, 3-benzyloxy-4-bromobenzyl, 4-bromo-3-methoxybenzyl, 2-nitrobenzyl, 3-nitrobenzyl, 4-nitrobenzyl, 2-methoxycarbonylmethylbenzyl, 3-methoxycarbonylmethylbenzyl, 4-methoxycarbonylmethylbenzyl groups, etc.

As preferred phenethyl groups wherein 1 to 3, optional hydrogen atom(s) on the benzene ring may be replaced by a lower alkoxy group or benzyloxy group, there can, for example, be mentioned phenethyl, 2-methoxyphenethyl, 3-methoxyphenethyl, 4-methoxyphenethyl, 2-benzyloxyphenethyl, 3-benzyloxyphenethyl, 4-benzyloxyphenethyl, 3,4-dimethoxyphenethyl, 3,5-dimethoxyphenethyl, 3,4,5-trimethoxyphenethyl, 3-benzyloxy-4-methoxyphenethyl, 4-benzyloxy-3-methoxyphenethyl groups, etc.

Specific examples of the compounds of the formula [I] as the first embodiment of this invention are shown in Table 1.

TABLE 1

| Compound No. | $R^1$ | $R^2$ | $R^3$ |
|---|---|---|---|
| 1 | Me | Me | $C_6H_5CH_2$ |
| 2 | Me | Me | $(4\text{-}MeOC_6H_4)CH_2$ |
| 3 | Me | Me | $(3\text{-}MeOC_6H_4)CH_2$ |
| 4 | Me | Me | $(2\text{-}MeOC_6H_4)CH_2$ |
| 5 | Me | Me | $(4\text{-}BnOC_6H_4)CH_2$ |
| 6 | Me | Me | $(3\text{-}BnOC_6H_4)CH_2$ |
| 7 | Me | Me | $(2\text{-}BnOC_6H_4)CH_2$ |
| 8 | Me | Me | $(4\text{-}FC_6H_4)CH_2$ |
| 9 | Me | Me | $(4\text{-}BrC_6H_4)CH_2$ |
| 10 | Me | Me | $(4\text{-}ClC_6H_4)CH_2$ |
| 11 | Me | Me | $(4\text{-}NO_2C_6H_4)CH_2$ |
| 12 | Me | Me | $(3\text{-}NO_2C_6H_4)CH_2$ |
| 13 | Me | Me | $(2\text{-}NO_2C_6H_4)CH_2$ |
| 14 | Me | Me | $(4\text{-}MeO_2CCH_2C_6H_4)CH_2$ |
| 15 | Me | Me | $(3\text{-}MeO_2CCH_2C_6H_4)CH_2$ |
| 16 | Me | Me | $(2\text{-}MeO_2CCH_2C_6H_4)CH_2$ |
| 17 | Me | Me | $(2,5\text{-diMeO}-C_6H_3)CH_2$ |
| 18 | Me | Me | $(2,6\text{-diMeO}-C_6H_3)CH_2$ |
| 19 | Me | Me | $(3,5\text{-diMeO}-C_6H_3)CH_2$ |
| 20 | Me | Me | $(3,4\text{-diMeO}-C_6H_3)CH_2$ |
| 21 | Me | Me | $(3\text{-}BnO,4\text{-}MeOC_6H_3)CH_2$ |
| 22 | Me | Me | $(4\text{-}BnO,3\text{-}MeOC_6H_3)CH_2$ |
| 23 | Me | Me | $(3\text{-}Br,4\text{-}MeOC_6H_3)CH_2$ |
| 24 | Me | Me | $(4\text{-}Br,3\text{-}MeOC_6H_3)CH_2$ |
| 25 | Me | Me | $(3,4\text{-diBnO}-C_6H_3)CH_2$ |
| 26 | Me | Me | $(3,4,5\text{-triMeO}-C_6H_2)CH_2$ |
| 27 | Me | Me | $(4\text{-}EtOC_6H_4)CH_2$ |
| 28 | Me | Me | $(4\text{-}PrOC_6H_4)CH_2$ |
| 29 | Me | Me | $(4\text{-}MeOC_6H_4)CH_2CH_2$ |
| 30 | Me | Me | $(3\text{-}MeOC_6H_4)CH_2CH_2$ |
| 31 | Me | Me | $(2\text{-}MeOC_6H_4)CH_2CH_2$ |
| 32 | Me | Me | $(4\text{-}BnOC_6H_4)CH_2CH_2$ |
| 33 | Me | Me | $4\text{-}PyCH_2$ |
| 34 | Me | Me | $3\text{-}PyCH_2$ |
| 35 | Me | Me | $2\text{-}PyCH_2$ |
| 36 | Me | Me | H |
| 37 | Me | Me | Et |
| 38 | Me | Me | Pr |
| 39 | Me | Me | Bu |
| 40 | $-CH_2-$ | | $C_6H_5CH_2$ |
| 41 | $-CH_2-$ | | $(4\text{-}MeOC_6H_4)CH_2$ |
| 42 | $-CH_2-$ | | $(3\text{-}MeOC_6H_4)CH_2$ |
| 43 | $-CH_2-$ | | $(2\text{-}MeOC_6H_4)CH_2$ |
| 44 | $-CH_2-$ | | $(4\text{-}BnOC_6H_4)CH_2$ |
| 45 | $-CH_2-$ | | $(3,4\text{-diMeO}-C_6H_3)CH_2$ |
| 46 | $-CH_2-$ | | $(3\text{-}BnO,4\text{-}MeOC_6H_3)CH_2$ |
| 47 | $-CH_2-$ | | $(3\text{-}Br,4\text{-}MeOC_6H_3)CH_2$ |
| 48 | $-CH_2-$ | | $(4\text{-}MeOC_6H_4)CH_2CH_2$ |
| 49 | $-CH_2-$ | | H |
| 50 | $-CH_2-$ | | Me |
| 51 | $-CH_2-$ | | Et |
| 52 | $-CH_2-$ | | Pr |
| 53 | Et | Et | $C_6H_5CH_2$ |
| 54 | Et | Et | $(4\text{-}MeOC_6H_4)CH_2$ |
| 55 | Et | Et | $(4\text{-}BnOC_6H_4)CH_2$ |
| 56 | Et | Et | H |
| 57 | Pr | Pr | $(4\text{-}MeOC_6H_4)CH_2$ |
| 58 | Pr | Pr | H |
| 59 | $^iPr$ | $^iPr$ | $(4\text{-}MeOC_6H_4)CH_2$ |
| 60 | $^iPr$ | $^iPr$ | H |
| 61 | Bn | Bn | $(4\text{-}MeOC_6H_4)CH_2$ |
| 62 | Bn | Bn | $(3\text{-}MeOC_6H_4)CH_2$ |
| 63 | Bn | Bn | $(2\text{-}MeOC_6H_4)CH_2$ |
| 64 | Bn | Bn | $(3,4\text{-diMeO}-C_6H_3)CH_2$ |

TABLE 1-continued $$R^1O \diagdown\diagup\diagdown\diagup\diagdown \diagup\diagdown$$
$$R^2O\diagup\diagdown\diagup N$$
$$HO \quad R^3$$ [I]

| Compound No. | R¹ | R² | R³ |
|---|---|---|---|
| 65 | Bn | Bn | H |
| 66 | Me | Bn | (4-MeOC₆H₄)CH₂ |
| 67 | Bn | Me | (4-MeOC₆H₄)CH₂ |

Abbreviations in the above have the following meanings.
Me: methyl group
Et: ethyl group
Pr: propyl group
Bu: butyl group
Bn: benzyl group
Py: pyridyl group
4-MeOC₆H₄, etc.: 4-methoxyphenyl, etc.

As the salts of the compounds of the formula [I], there can usually be mentioned hydrohalides, such as hydrochlorides, hydrobromides, preferable hydrochlorides, but they may be other salts, for example oxalates, tartrates, etc.

Next, description is made on a process for preparation of the compounds of the formula [III] as the second embodiment of this invention.

The compounds of the formula [III] can be prepared by either of the following Preparation process A and Preparation process B.

[Structures of compounds II, I-a, and III shown with arrows labeled "First step" and "Second step"]

This preparation process is characterized by a regioselective cyclization of a compound represented by the formula [II] at the ortho position of the phenolic hydroxyl group in the presence of a phosphoric acid halide to give a compound represented by the formula [I-a] or a salt thereof (first step), and then reducing the compound represented by the formula [I-a] or the salt (second step).

The reaction in the first step can be carried out in a halogenated hydrocarbon such as dichloromethane, chloroform, dichloroethane, carbon tetrachloride or chlorobenzene; an aromatic hydrocarbon such as benzene, toluene or xylene; or an aprotic polar solvent such as acetonitrile, propionitrile, dimethyl sulfoxide, N,N-dimethylformamide or sulfolane; or the like using the phosphoric acid halide in an amount of usually 1 to 100 moles, preferably 1 to 3 moles per mole of the compound of the formula [II]. The reaction temperature is usually from room temperature to the boiling point of the solvent used, preferably from room temperature to 60° C., and this reaction is usually completed in 1 to 36 hours.

As the phosphoric acid halide, there can, for example, be mentioned phosphoryl chloride(POCl₃), phosphorus pentachloride (PCl₅), phosphoryl bromide (POBr₃) or the like.

After completion of the reaction, the crude hydrohalide, e.g. hydrochloride of the compound of the formula [I-a] can be obtained by removing the solvent under reduced pressure. The compound of the formula [I-a] or its hydrohalide can be used without a further purification in the following step, but preferably, it is good for enhancement of its yield to subject it to usual purifications such as a recrystallization and/or a column chromatography.

The compounds of the formula [I-a] or their hydrohalides can be converted to various salts such as oxalates and tartrates according to a usual process, but as salts of the compounds of the formula [I-a], hydrochlorides and hydrobromides, particularly hydrochlorides are preferable.

The reaction in the second step can be carried out in an alcohol solvent such as methanol or ethanol, using a reducing agent in an amount of 1 to 5 moles, preferably 1 to 2 moles per mole of the compound of the formula [I-a] or a salt thereof. The reaction temperature is from 0° C. to room temperature, and this reaction is completed in 10 minutes to one hour.

As the reducing agent, there can, for example, be mentioned sodium borohydride, sodium cyanoborohydride or the like.

The compound of the formula [III] or a salt thereof can be obtained by a recrystallization of the residue obtained by removing the solvent under reduced pressure after completion of the reaction.

The compounds of the formula [III] or their salts can be converted to various salts by a conventional manner.

As salts of the compounds of the formula [III], there can, for example, be mentioned hydrochlorides, hydrochlorides, hydrobromides, oxalates, tartrates or the like, preferably hydrochlorides.

The fact that comounds of the formula [III] thus obtained have a phenolic hydroxyl group at the 8-position was confirmed by leading them to known compounds (e.g., dl-corpaverine, anhalamine, etc.) as shown in Examples and Reference examples and also by measuring heteronuclear multi bond connectivity (HMBC) in NMR.

Preparation Process B

[Structures of compounds I-a and III shown with arrow]

This preparation process is characterized by a reduction of a compound represented by the formula [I-a] or a salt thereof to give a compound of the formula [III] or a salt thereof.

This step can be carried out in the same manner as in the second step of Preparation process A.

The third embodiment of this invention, i.e. a process for preparation of compounds of the formula [I-a] is described below.

The compounds of the formula [I-a] can be prepared by the following Preparation process C.

Preparation Process C

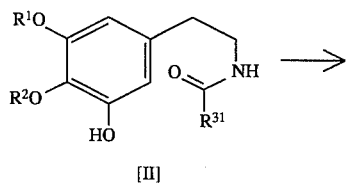

[II]

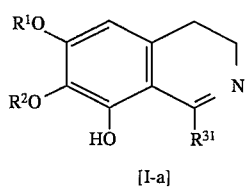

[I-a]

This preparation process is characterized by a regioselective cyclization of a compound represented by the formula [II] in the presence of a phosphoric acid halide at the ortho position of the phenolic hydroxyl group to give a compound represented by the formula [I-a] or a salt thereof.

This step can be carried out in the same manner as in the first step of Preparation process A.

The raw material phenethylamide derivatives represented by the formula [II] can be prepared according to a known process (see, for example, *Chem. Pharm. Bull.* 15(6), 879, 1967). Namely, a phenethylamide derivative of the formula [II] can be prepared by condensing a phenethylamine derivative represented by the formula

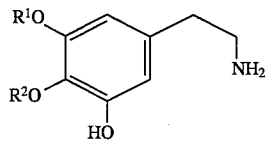

wherein $R^1$ and $R^2$ are as defined above, with a compound represented by the formula

wherein $R^{31}$ is as defined above, and X denotes a halogen atom, hydroxyl group or lower alkyloxy group.

The cyclization reaction of the first step of Preparation step A in the second embodiment of this invention and the cyclization reaction of Preparation step C in the third embodiment thereof regioselectively progress. The reason is considered to lie, although it is not intended to be bound thereto, in a combination of the condition that each reaction is carried out without protecting the phenolic hydroxyl group and the condition that the reaction is carried out in the presence of a phosphoric acid halide. In this connection, the aforesaid prior art literatures do not suggest such a combination of the conditions and effects obtained thereby at all.

The fourth embodiment of this invention relates to use of the compounds of the formula [I-a] for preparation of the compounds of the formula [III]. As above mentioned, the compounds of the formula [I-a] can be used as a raw material or synthesis of the compounds of the formula [III] useful as synthetic intermediates for antitumor effect potentiators.

All publications cited in this specification are herein incorporated by reference as if each publication was specifically and individually indicated to be incorporated by reference.

This invention is more specifically described below according to examples, but it is a matter of course that this invention is not limited to these examples.

EXAMPLE 1

1-1) 3,4-Dihydro-6,7-dimethoxy-1-(4-methoxybenzyl) isoquinolin-8-ol hydrochloride Phosphoryl chloride (5.42 ml, 58.1 mmol) was added to a chloroform (100 ml) solution of N-(4,5-dimethoxy-3-hydroxyphenethyl)-4-methoxyphenylacetamide (6.71 g, 19.4 mmol) at room temperature, and the mixture was stirred under a nitrogen atmosphere at 55° C. for 16 hours. The solvent and excess phosphoryl chloride were removed under reduced pressure, and the resultant residue was recrystallized from methanol-ether to give 6.05 g (yield: 86%) of the captioned compound as colorless needles.

Melting point: 214°–216° C. (dec)

High resolution FAB-MS (m/z, $(C_{19}H_{21}NO_4+H)^+$):

Calc. 328.1549

Found 328.1526

$^1$H-NMR (300 MHz, CDCl$_3$, δ ppm): 2.85 (2H, t, J=7.4 Hz), 3.73 (3H), s), 3.82 (2H, t, J=7.4 Hz), 3.91 (3H, s), 3.94 (3H, s), 4.78 (2H, s), 6.38 (1H, s), 6.76(2H, d, J=8.8 Hz), 7.40 (2H, d, J=8.8 Hz)

1-2) 6,7-Dimethoxy-1-(4-methoxybenzyl)-1,2,3,4-tetrahydroisoquinolin-8-ol

Sodium borohydride (292 mg, 7.72 mmol) was added to a methanol (40 ml) solution of the compound (2.10 g, 5.77 mmol) obtained in 1—1 under ice cooling, and the mixture was stirred for 40 minutes. The solvent was removed under reduced pressure, bring (200 ml) was added to the resultant residue, and the mixture was extracted three times with chloroform (100 ml). The organic layer was dried over anhydrous magnesium sulfate and the solvent was removed under reduced pressure to give 1.82 g (yield: 96%) of the captioned compound as a colorless solid.

High resolution FAB-MS (m/z, $(C_{19}H_{23}NO_4+H)^+$):

Calc. 330.1706

Found 330.1736

$^1$H-NMR (300 MHz, CDCl$_3$, δ ppm): 2.62 (1H), ddd, J=3.0 Hz, 4.2 Hz, 15.9 Hz), 280–2.92 (1H, m), 2.83 (1H, dd, J=10.0 Hz, 13.9 Hz), 2.98 (1H, ddd, J=3.0 Hz, 5.8 Hz, 12.1 Hz), 3.21 (1H, ddd, J=4.2 Hz, 10.8 Hz, 12.1 Hz), 3.25 (1H, dd, J=2.9 Hz, 13.9 Hz), 3.80 (3H, s), 3.84 (3H, s), 3.87 (3H, s), 4.29 (1H, dd, J=2.9 Hz, 10.0 Hz), 6.23 (1H, s), 6.87 (2H, d, J=8.9 Hz), 7.20 (2H, d, J=8.9 Hz)

The same operations as in Example 1 were carried out in the following Examples 2 to 14 to obtain the respective captioned compounds.

EXAMPLE 2

2-1) 3,4-Dihydro-6,7-dimethoxyisoquinolin-8-ol hydrochloride 1.78 g (yield: 69%) of the captioned compound was obtained as colorless needles using N-(4,5-dimethoxy-3-hydroxyphenethyl) formamide (2.40 g, 10.7 mmol) as a raw material.

Melting point: 226°–228° C. (dec)

$^1$H-NMR (300 MHz, CD$_3$OD, δ ppm):

3.09 (2H, dt, J=1.1 Hz, 8.0 Hz), 3.78 (3H, s), 3.83 (2H, dt, J=1.1 Hz, 8.0 Hz), 4.00 (3H, s), 6.67 (1H, s), 8.90 (1H, s)

2-2) 6,7-Dimethoxy-1,2,3,4-tetrahydroisoquinolin-8-ol (anhalamine)

0.94 g (yield: 99%) of the captioned compound was obtained as a colorless solid using as a raw material the compound (1.10 g, 4.51 mmol) obtained in 2-1.

Melting point: 186°–188° C.

High resolution FAB-MS (m/z, (C$_{11}$H$_{15}$NO$_3$+H)$^+$):

Calc. 210.1130

Found 210.1119

$^1$H-NMR (300 MHz, CDCl$_3$-CD$_3$OD, δ ppm): 2.7 (2H, t, J=6.0 Hz), 3.06 (2H, t, J=6.0 Hz,), 3.84 (6H, s), 3.90 (2H, s), 6.22 (1H, s)

EXAMPLE 3

3-1) 3,4-Dihydro-6,7-dimethoxy-1-(3-methoxybenzyl) isoquinolin-8-ol hydrochloride 1.78 g (yield: 75%) of the captioned compound was obtained as colorless needles using N-(4,5-dimethoxy-3-hydroxyphenethyl)-3-methoxyphenylacetamide (2.27 g, 6.57 mmol) as a raw material.

Melting point: 162°–169° C.

High resolution FAB-MS (m/z, (C$_{19}$H$_{21}$NO$_4$+H)$^+$):

Calc. 328.1549

Found 328.1529

$^1$H-NMR (300 MHz, CDCl$_3$, δ ppm):

2.87 (2H, t, J=7.3 Hz), 3.78 (3H, s), 3.84 (2H, t, J=7.3 Hz), 3.91 (3H, s), 3.94 (3H, s), 4.83 (2H, s), 6.39 (1H, s), 6.74 (1H, dd, J=2.1 Hz, 7.9 Hz), 7.01 (1H, dd J=2.1 Hz, 7.9 Hz), 7.08 (1H, t, J=2.1 Hz), 7.14 (1H, t, J=7.9 Hz)

3-2) 6,7-Dimethoxy-1-(3-methoxybenzyl)-1,2,3,4-tetrahydroisoquinolin-8-ol 1.53 g (yield: 99%) of the captioned compound was obtained as a colorless solid using as a raw material 1.70 g (4.67 mmol) of the compound obtained in 3-1.

Melting point: 153.5°–155.5° C.

FAB-MS (m/z, (C$_{19}$H$_{23}$NO$_4$+H)$^+$): 330

$^1$H-NMR (300 MHz, CDCl$_3$, δ ppm): 2.60 (1H, td like, J=3.4 Hz, 19.5 Hz), 2.77–2.87 (2H, m), 2.94 (1H, ddd, J=2.9 Hz, 5.9 Hz, 12.1 Hz), 3.18–3.29 (2H, m), 3.81 (3H, s), 3.83 (3H, s), 3.87 (3H, s), 4.29 (1H, dd, J=2.7 Hz, 10.4 Hz), 6.23 (1H, s), 6.77 (1H, dd, J=2.4 Hz, 7.1 Hz), 6.84–6.87 (1H, m), 6.89 (1H, d, J=7.5 Hz), 7.24 (1H, t, J=7.5 Hz)

EXAMPLE 4

4-1) 3,4-Dihydro-6,7-dimethoxy-1-(2-methoxybenzyl) isoquinolin-8-ol hydrochloride 498 mg (yield: 79%) of the captioned compound was obtained as colorless needles using as a raw material N-(4,5-dimethoxy-3-hydroxyphenethyl)-2-methoxyphenylacetamide (601 mg, 1.74 mmol).

Melting point: 147°–150° C.

FAB-MS (m/z, (C$_{19}$H$_{21}$NO$_4$+H)$^+$): 328

$^1$H-NMR (300 MHz, CDCl$_3$, δ ppm): 2.92 (2H, t, J=7.3 Hz), 3.87 (2H, t, J=7.3 Hz), 3.81 (3H, s), 3.83 (3H, s), 3.94 (3H, s), 4.70 (2H, s), 6.41 (1H, s), 6.77–6.84 (2H, m), 7.13–7.21 (2H, m)

4-2) 6,7-Dimethoxy-1-(2-methoxybenzyl)-1,2,3,4-tetrahydroisoquinolin-8-ol 245 mg (yield: 90%) of the captioned compound was obtained as a colorless solid using as a raw material the compound (300 mg, 0.824 mmol) obtained in 4-1.

FAB-MS (m/z, (C$_{19}$H$_{23}$NO$_4$+H)$^+$): 330

$^1$H-NMR (300 MHz, CDCl$_3$, δ ppm): 2.58–2.65 (1H, m), 2.80–3.00 (2H, m), 2.98 (1H, dd, J=10.5 Hz, 14.0 Hz), 3.18 (1H, dd, J=2.7 Hz, 13.7 Hz), 3.31 (1H, m), 3.84 (3H, s), 3.87 (3H, s), 3.8 (3H, s), 4.31 (1H, dd, J=2.5 Hz, 10.4 Hz), 6.24 (1H, s), 6.90–6.97 (2H, m), 7.20–7.23 (2H, m)

EXAMPLE 5

5-1) 3,4-Dihydro-6,7-dimethoxy-1-(3,4-dimethoxybenzyl) isoquinolin- 8-ol hydrochloride 642 mg (yield: 79%) of the captioned compound was obtained as colorless needles using as a raw material N-(4,5-dimethoxy-3-hydroxyphenethyl)-3,4-dimethoxyphenylacetamide (771 mg, 2.05 mmol).

Melting point: 217°–220° C.

FAB-MS (m/z, (C$_{20}$H$_{23}$NO$_5$+H)$^+$): 358

$^1$H-NMR (300 MHz, CD$_3$OD, δ ppm): 2.97–3.01 (2H, m), 3.68–3.80 (2H, m), 3.76 (3H, s), 3.80 (3H, s), 3.80 (3H, s), 3.96 (3H, s), 4.56 (2H, s), 6.67 (1H, s), 6.82–6.94 (3H, m)

5-2) 6,7-Dimethoxy-1-(3,4-dimethoxybenzyl)-1,2,3,4-tetrahydroisoquinolin- 8-ol 255 mg (yield: 94%) of the captioned compound was obtained as a colorless solid using as a raw material the compound (298 mg, 0.756 mmol) obtained in 5-1

FAB-MS (m/z, (C$_{20}$H$_{25}$NO$_5$+H)$^+$): 360

$^1$H-NMR (300 MHz, CDCl$_3$, δppm): 2.56–2.62 (1H, m), 2.74–2.85 (2H, m), 2.82 (1H, dd, J=10.0 Hz, 13.6 Hz), 2.89–2.62 (1H, m), 3.17–3.26 (1H, m), 3.22 (1H, dd, J=2.9 Hz, 13.7 Hz), 3.84 (3H, s), 3.87 (3H, s), 3.89 (3H, s), 4.27 (1H, dd, J=2.9 Hz, 10.0 Hz), 6.23 (1H, s), 6.79–6.84 (3H, m)

EXAMPLE 6

6-1) 3,4-Dihydro-6,7-dimethoxy-1-(3,5-dimethoxybenzyl)isoquinolin- 8-ol hydrochloride 443 mg (yield: 70%) of the captioned compound was obtained as colorless needles using as a raw material N-(4,5-dimethoxy -3-hydroxyphenethyl)-3,5-dimethoxyphenylacetamide (607 mg, 1.62 mmol).

Melting point: 192°–194° C.

FAB-MS (m/z, (C$_{20}$H$_{23}$NO$_5$+H)$^+$): 358

$^1$H-NMR (300 MHz, CDCl$_3$, δ ppm): 2.87 (2t, J=7.4 Hz), 3.76 (6H, s), 3.77–3.88 (2H, m), 3.91 (3H, s), 3.95 (3H, s), 4.79 (2H, s), 6.30 (1H, t, J=2.1 Hz), 6.40 (1H, s), 6.68 (2H, d, J=2.1 Hz)

6-2) 6,7-Dimethoxy-1-(3,5-dimethoxybenzyl)-1,2,3, 4-tetrahydroisoquinolin- 8-ol 90 mg (yield: 98%) of the captioned compound was obtained as colorless solid using as a raw material the compound (101 mg, 0.256 mmol) obtained in 6-1.

Melting point: 139°–142° C.

FAB-MS (m/z, (C$_{20}$H$_{25}$NO$_5$+H)$^+$): 360

$^1$H-NMR (300 MHz, CDCl$_3$, δ ppm): 2.58–2.65 (1H, m), 2.79 Hz), 1H, dd, J=10.3 Hz, 13.6 Hz), 2.76–2.97 (2H, m), 3.17–3.23 (1H, m), 3.23 (1H, dd, J=10.3 Hz, 13.6 Hz), 2.76–2.97 (2H, m), 3.17–3.23 (1H, m), 3.23 (1H, dd, J=2.7 Hz, 13.6 Hz), 3.80 (6H, s), 3.84 (3H, s), 3.89 (3H, s), 4.30 (1H, dd, J=2.7 Hz, 10.3 Hz), 6.23 (1H, s), 6.35 (1H, t, J=2.2 Hz), 6.40 (2H, d, J=2.2 Hz)

EXAMPLE 7

7-1) 3,4-Dihydro-6,7-dimethoxy-1-(2,5-dimethoxy-benzyl) isoquinolin-8-ol hydrochloride 553 mg (yield: 80%) of the captioned compound was obtained as colorless solid using as a raw material N-(4,5-dimethoxy -3-hydroxyphenethyl)-2,5-dimethoxyphenylacetamide (659 mg, 1.75 mmol).

Melting point: 205.0°–207.5° C. (dec)

High resolution FAB-MS (m/z, (C$_{20}$H$_{23}$NO$_5$+H)$^+$):
Calc. 358.1655
Found 358.1626

$^1$H-NMR (300 MHz, CDCl$_3$, δ ppm): 2.98 (2H, t, J=7.3 Hz), 3.68 (2H, t, J=7.3 Hz, 3.74 Hz), (3H, s), 3.75 (3H, s), 3.97 (3H, s), 4.51 (2H, s), 6.67 (1H, s), 6.83–7.02 (3H, m)

7-2) 6,7-Dimethoxy-1-(2,5-dimethoxybenzyl)-1,2,3, 4-tetrahydroisoquinolin-8-ol 272 mg (yield: 99%) of the captioned compound was obtained as a colorless solid using as a raw material the compound (300 mg, 0.726 mmol) obtained in7-1.

FAB-MS (m/z, (C$_{20}$H$_{25}$NO$_5$+H)$^+$): 360

$^1$H-NMR (300 MHz, CDCl$_3$, δppm): 2.56–2.67 (1H, m), 2.77–3.02 (3H, m), 3.14 (1H, dd, J=2.7 Hz, 13.7 Hz), 3.29 (1H, dt, J=4.5 Hz, 11.9 Hz), 3.78 (3H, s),3.84 (6H, s), 3.88 (3H, s), 4.31 (1H, dd, J=2.7 Hz, 10.2 Hz), 6.24 (1H, s), 6.74 (1H, dd, J=2.9 Hz, 8.7 Hz), 6.80–6.89 (2H, m)

EXAMPLE 8

8-1) 3,4-Dihydro-6,7-dimethoxy-1-(3,4,5-trimethoxybenzyl)isoquinolin-8-ol hydrochloride 450 mg (yield: 61%) of the captioned compound was obtained as colorless needles using as a raw material N-(4,5-dimethoxy -3-hydroxyphenethyl)-3,4,5-trimethoxyphenylacetamide (700 mg, 1.73 mmol).

Melting point: 206°–212° C.

FAB-MS (m/z, (C$_{21}$H$_{25}$NO$_6$+H)$^+$): 388

$^1$H-NMR (300 MHz, CDCl$_3$, δppm): 2.80–2.91 (2H, m), 3.78 (3H, s), 3.82 (3H, s), 3.83 (3H, s), 3.93 (3H, s), 3.96 (3H, s), 3.75–3.88 (2H, m), 4.79 (2H, s), 6.41 (1H, s), 6.86 (2H, s)

8-2) 6,7-Dimethoxy-1-(*3,4,5-trimethoxybenzyl)-1, 2,3, 4-tetrahydroisoquinolin-8-ol 43 mg (yield: 100%) of the captioned compound was obtained as a colorless solid using as a raw material the compound (47 mg, 0.11 mmol) obtained in 8-1.

FAB-MS (m/z, (C$_{21}$H$_{27}$NO$_6$+H)$^+$): 390

$^1$H-NMR (300 MHz, CDCl$_3$, δppm): 2.60 (1H, td, J=3.8 Hz, 16.1 Hz, 2.74–2.88 (1H, m), 2.81 (1H, dd, J=10.0 Hz, 14.0 Hz), 2.90–3.00 (1H, m), 3.15–3.20 (1H, m), 3.24 (1H, dd, J=2.7 Hz, 10.0 Hz), 3.84 (6H, s), 3.86 (6H, s), 3.89 (3H, s), 4.30 (1H, dd, J=2.7 Hz, 10.0 Hz), 6.24 (1H, s), 6.49 (2H, s)

EXAMPLE 9

9-1) 3,4-Dihydro-6,7-dimethoxy-1-(4-nitrobenzyl) isoquinolin-8-ol hydrochloride 425 mg (yield: 82%) of the captioned compound was obtained as colorless needles using as a raw material N-(4, 5-dimethoxy -3-hydroxyphenethyl)-4-nitrophenylacetamide (495 mg, 1.37 mmol).

Melting point: 129°–131° C.

FAB-MS (m/z, (C$_{18}$H$_{18}$N$_2$O$_5$+H)$^+$): 343

$^1$H-NMR (300 MHz, CD$_3$OD, δppm): 3.08 (2H, td, J=7.7 Hz), 3.81 (2H, t, J=7.7 Hz), 3.97 (3H, s), 4.70 (2H, s), 6.70 (1H, s), 7.52–7.55 (2H, m), 8.19–8.22 (2H, m)

9-2) 6,7-Dimethoxy-1-)4-nitrobenzyl)-1,2,3,4-tetrahydroisoquinolin-8-ol 49 mg (yield: 89%) of the captioned compound was obtained as a colorless solid using as a raw material the compound (61 mg, 0.16 mmol) obtained in 9-1.

FAB-MS (m/z, (C$_{18}$H$_{20}$N$_2$O$_5$+H)$^+$): 345

$^1$H-NMR (300 MHz, DMSO-d$_6$, δ ppm): 2.45–2.58 (2H, m), 2.80–2.92 (1H, m), 3.06–3.14 (1H, m), 3.26–3.45 (2H, m), 3.65 (3H, s), 3.73 (3H, s), 3.76 (1H, brs), 4.00–4.08 (1H, m), 6.23 (1H, s), 7.49–7.54 (2H, m), 8.14–8.21 (2H, m), 8.95 (1H, s)

EXAMPLE 10

10-1) 3,4-Dihydro-6,7-dimethoxy-1-(3-nitrobenzyl) isoquinolin-8-ol hydrochloride 431 mg (yield: 85%) of the captioned compound was obtained as colorless needles using as a raw material N-(4, 5-dimethoxy -3-hydroxyphenethyl)-3-nitrophenylacetamide (481 mg, 1.34 mmol).

Melting point: 124°–127.5° C.

FAB-MS (m/z, (C$_{18}$H$_{18}$N$_2$O$_5$+H)$^+$): 343

$^1$H-NMR (300 MHz, CD$_3$OD, δ ppm): 3.03–3.08 (2H, m), 3.72 (3H, s), 3.77–3.82 (2H, m), 3.96 (3H, s), 4.72 (2H, s), 7.59 (1H, t, J=7.7 Hz), 7.70 (1H, dd, J=2.2 Hz, 7.7 Hz), 8.16–8.19 (1H, m), 8.23–8.24 (1H, m)

10-2) 6,7-Dimethoxy-1-(3-nitrobenzyl)-1,2,3,4-tetrahydroisoquinolin-8-ol 51 mg (yield: 92%) of the captioned compound was obtained as a colorless solid using as a raw material the compound (61 mg, 0.16 mmol) obtained in 10-1.

FAB-MS (m/z, (C$_{18}$H$_{20}$N$_2$O$_5$+H$^+$): 345

$^1$H-NMR (300 MHz, CDCl$_3$-CD$_3$OD, δ ppm): 2.63–2.95 (4H, m), 3.03 (1H, dd, J=9.5 Hz, 13.8 Hz), 3.13–3.26 (1H, m), 3.77 (3H, s), 3.80 (3H, s), 4.31 (1H, dd, J=2.9 Hz, 9.5

Hz), 6.28 (1H, s), 7.54 (1H, t, J=7.9 Hz), 7.68–7.73 (1H, m), 8.06–8.12 (1H, m), 8.16 (1H, t, J=1.8 Hz).

EXAMPLE 11

11-1) 2-[2-{(3,4-Dihydro-6,7-dimethoxy-8-hydroxy-isoquinolin- 1-yl)methyl}phenyl]acetic acid methyl ester hydrochloride 731 mg (yield: 64%) of the captioned compound was obtained as colorless needles using as a raw material 2-[2-[2-[{2-(3, 4-dimethoxy-5-hydroxyphenyl)ethyl}amino]-2-oxoethyl} phenyl}acetic acid methyl ester (1.09 g, 2.82 mmol).

Melting point: 112°–115° C.

FAB-MS (m/z, $(C_{21}H_{23}NO_5H)^+$): 370

$^1$H-NMR (300 MHz, CDCl$_3$, δ ppm): 2.96–3.07 (2H, m), 3.74 (3H, s), 3.81 (3H, m), 3.83 (2H, s), 3.87– 3.94 (2H, m), 3.96 (3H, s), 4.81 (2H, s), 6.45 (1H,s), 6.89 (1H, d, J =7.3 Hz), 7.08 (1H, dt, J=1.7 Hz, 7.3 Hz), 7.15–7.24 (2H, m)

11-2) 2-[2-{(6,7-Dimethoxy-8-hydroxy-1,2,3,4-tetrahydroisoquinolin-1-yl)methyl}phenyl]acetic acid methyl ester 253 mg (yield: 92%) of the captioned compound was obtained as a colorless solid using as a raw material the compound (303 mg, 0.745 mmol) obtained in 11-1.

FAB-MS (m/z, $(C_{21}H_{25}NO_5+H^+)$: 372

$^1$H-NMR (300 MHz, CDCl$_3$, δ ppm): 2.60–2.70 (1H, m), 2.84 (1H, dd, J=11.0 Hz, 14.2 Hz), 2.80–2.90 (1H, m), 2.99 (1H, ddd, J=2.4Hz, 5.8 Hz, 11.9 Hz), 3.26 (1H, dd, J=4.1 Hz, 11.0 Hz), 3.34 (1H, dd, J=2.6 Hz, 13.9 Hz), 3.68 (3H, s), 3.85 (3H, s), 3.89 (3H, s), 3.86 (1H, d, J=15.2 Hz), 4.03 (1H, d, J=15.2 Hz), 4.22 (1H, dd, J=2.4 Hz, 11.0 Hz), 6.25 (1H, s), 7.19–7.30 (4H, m)

EXAMPLE 12

12-1) 3,4-Dihydro-6,7-dimethoxy-1-(3-pyridylmethyl) isoquinolin-8-ol dihydrochloride 1.17 g (yield: 82%) of the captioned compound was obtained as colorless needles using as a raw material N-(4, 5-dimethoxy -3-hydroxyphenethyl)-3-pyridylacetamide (1.22 g, 3.87 mmol).

High resolution FAB-MS (m/z, $(C_{17}H_{18}N_2O_3+H)^+$):

Calc. 299.1396

Found 299.1401

$^1$H-NMR (300 MHz, CD$_3$OD, δ ppm): 3.13 (2H, t, J=7.6 Hz), 3.73 (3H, s), 3.85 (2H, t, J=7.6 Hz), 3.99 (3H, s), 4.81 (2H, s), 6.75 (1H, s), 8.06 (1H, dd, J=5.8 Hz, 8.3 Hz), 8.57 (1H, d, J=8.3 Hz), 8.81 (1H, d, J=5.8 Hz), 8.93 (1H, s)

12-2) 6,7-Dimethoxy-1-(3-pyridylmethyl)-1,2,3,4-tetrahydroisoquinolin-8-ol 716 mg (yield: 83%) of the captioned compound was obtained as colorless solid using as a raw material the compound (1.06 g, 2.86 mmol) obtained in 12-1.

Melting: 190°–191.5° C.

High resolution FAB-MS (m/z, $(C_{17}H_{18}N_2O_3+H)^+$):

Calc. 301.1552

Found 301.1534

$^1$H-NMR (300 MHz, CD$_3$OD, δ ppm): 2.68 (1H, td, J=4.1 Hz, 17.0 Hz), 2.81 (1H, ddd, J=5.9 Hz, 10.1 Hz, 17.0 Hz), 2.90–3.00 (1H, m), 2.99 (1H, dd, J=9.2 Hz, 14.5 Hz), 3.15–3.35 (2H, m), 3.77 (3H, s), 3.81 (3H, s), 4.36 (1H, dd, J=2.9 Hz, 9.2 Hz), 6.30 (1H, s), 7.39 (1H, dd, J=4.9 Hz, 7.8 Hz), 7.78 (1H, d, J=7.8 Hz), 8.40 (1H, dd, J=1.8 Hz, 4.9 Hz), 8.46 (1H, d, J=1.8 Hz)

EXAMPLE 13

13-1) 3,4-Dihydro-6,7-dimethoxy-1-propylisoquinolin-8-ol hydrochloride 332 mg (yield: 72%) of the captioned compound was obtained as colorless needles using as a raw material N-(4, 5-dimethoxy -3-hydroxyphenethyl) butanamide (430 mg, 1.61 mmol).

Melting point: 187°–191° C.

FAB/MS (m/z, $(C_{14}H_{19}NO_3+H^+)$: 250

$^1$H-NMR (300 MHz, CD$_3$OD, δ ppm): 0.96 (3H, t, J=7.4 Hz), 1.67 (2H, sex, J=7.0 Hz), 3.09 (2H, t, J=7.4 Hz), 3.55–3.67 (2H, m), 3.71 (3H, s), 3.90 (3H, s), 6.61 (1H, s)

13-2) 7-Dimethoxy-1-propyl-1,2,3,4-tetrahydroisoquinolin- 8-ol 191 mg (yield: 99%) of the captioned compound was obtained as a colorless solid using as a raw material the compound (220 mg, 0.770 mmol) obtained in 13-1.

FAB-MS (m/z, $(C_{14}H_{21}NO_3+H)^+$): 252

EXAMPLE 14

14-1) 3,4-Dihydro-6,7-dimethoxy-1-(4-methoxyphenethyl) isoquinolin-8-ol hydrochloride 478 g (yield: 71%) of the captioned compound was obtained as colorless needles using as a raw material N-(4, 5-dimethoxy -3-hydroxyphenethyl)-2-(4-methoxyphenyl) propanamide (640 mg, 1.78 mmol).

Melting point: 191.5°–193.0° C.

High resolution FAB-MS (m/z, $(C_{20}H_{23}NO_4+H)^+$):

Calc. 342.1706

Found 342.1710

$^1$H-NMR (300 MHz, CD$_3$OD, δ ppm): 2.85 (2H, t, J=7.5 Hz), 2.98 (2H, t, J=7.7 Hz), 3.45 (2H, t, J=7.7 Hz), 3.58 (2H, t, J=7.5 Hz), 3.75 (3H, s), 3.83 (3H, s), 4.00 (3H, s), 6.70 (1H, s), 6.83 (2H, d, J=8.5 Hz), 7.02 (2H, d, J=8.5 Hz)

14-2) 6,7-Dimethoxy-1-(4-methoxyphenethyl)-1,2,3, 4-tetrahydroisoquinolin-8-ol 280 mg (yield: 100%) of the captioned compound was obtained as a colorless solid using as a raw material the compound (300 mg, 0.794 mmol) obtained in 14-1.

FAB-MS (m/z, $(C_{20}H_{25}NO_4+H)^+$): 344

$^1$H-NMR (300 MHz, CDCl$_3$, δ ppm): 1.85–2.00 (1H, m), 2.10–2.22 (1H, m), 2.54–2.89 (4H, m), 2.94–3.04 (1H, m), 3.08—3.21 (1H, m), 3.78 (3H, s), 3.82 (3H, s), 3.85 (3H, s), 4.07 (1H, dd, J=2.4 Hz, 10.0 Hz), 6.19 (1H, s), 6.81 (2H, d, J=8.4 Hz), 7.17 (2H, d, J=8.4 Hz)

EXAMPLE 15

6,7-Dimethoxy-1-(40fluorobenzyl)-1,2,3,4-tetrahydroisoquinolin-8-ol

Phosphoryl chloride (370 μl, 3.97 mmol) was added to a chloroform (6 ml) solution of N-(4,5-dimethoxy-3-hydroxyphenethyl)- 4-fluorophenylacetamide (437 mg, 1.31 mmol) at room temperature, and the mixture was stirred under a nitrogen atmosphere at 55° C. for 8 hours. The solvent and the excess phosphoryl chloride were removed under reduced pressure and the resultant residue was dissolved in methanol (25 ml). Sodium borohydride (65 mg, 1.72 mmol) was added to this methanol solution under ice cooling and the mixture was stirred for 1 hour. The solvent was removed under reduced pressure, brine (50 ml) was added to the resultant residue, and the mixture was extracted three times with chloroform (390 ml). The organic layer was dried over anhydrous magnesium sulfate, the solvent was removed under reduced pressure, and the resultant residue was recrystallized from ethyl acetate-hexane to give 199 mg (yield: 48%) of the captioned compound as a colorless solid.

Melting point: 195°–200° C.

FAB-MS (m/z, $(C_{18}H_{20}NO_3F+H)^+$): 318

$^1$H-NMR (300 MHz, $CD_3OD$, δ ppm): 2.97–3.08 (3H, m), 3.22–3.34 (1H, m), 3.46–3.55 (2H, m), 3.78 (3H, (2H, m), 7.34–7.38 (2H, m)

The same operation as in Example 15 were carried out in the following Examples 16 and 17 to obtain the respective captioned compounds.

EXAMPLE 16

6,7-Diisopropoxy-1-(4-methoxybenzyl)-1,2,3,4-tetrahydroisoquinolin-8-ol 1.00 g (yield: 67%) of the captioned compound was obtained as a colorless solid using as a raw material N-(4,5-diisopropoxy-3-hydroxyphenethyl)-4-methoxyphenylacetamide (1.56 g, 3.89 mmol).

Melting point: 115°–120° C.

High resolution FAB-MS (m/z, $(C_{23}H_{31}NO_4+H)^{30}$):

Calc. 386.2332

Found 386.2332

$^1$H-NMR (300 MHz, $CDCl_3$, δ ppm): 1.28–1.35 (12H, m), 2.58 (1H, td, J=3.4 Hz, 15.9 Hz), 2.77–3.00 (3H, m), 3.20 (1H, dd, J=2.8 Hz, 13.5 Hz), 3.80 (3H, s), 4.24 (1H, dd, J=2.8 Hz, 10.1 Hz), 4.50 (1H, sep, J=6.1 Hz), 4.56 (1H, sep, J=6.1 Hz), 6.21 (1H, s), 6.86, (2H, d, J=8.5 Hz), 7.20 (2H, d, J=8.5 Hz)

EXAMPLE 17

1-(3-Methoxybenzyl)-6,7-methylenedioxy-1,2,3,4-tetrahydroisoquinolin-8-ol 306 mg (yield: 44%) of the captioned compound was obtained as a colorless solid using as a raw material N-(4,5-methylenedioxy- 3-hydroxyphenethyl)-3-methoxyphenylacetamide (730 mg, 2.22 mmol).

FAB-MS (m/z, $(C_{18}H_{19}NO_4+H)^+$): 314

$^1$H-NMR (300 MHz, $CDCl_3$-$CD_3OD$, δ ppm): 2.60–2.72 (1H, m), 2.80–3.06 (3H, m), 3.16–3.27 (1H, m), 3.31 (1H, dd, J=3.2 Hz, 13.9 Hz), 4.43 (1H, dd, J=2.9 Hz, 10.3 Hz), 5.81– 5.88 (2H, m), 6.23 (1H, s), 6.77–6.92 (3H, m), 7.26 (1H, t, J=7.7 Hz)

Reference Example 1

Synthesis of 6,7-dimethoxy-1-(4-methoxybenzyl)-2-methyl-1,2,3,4-tetrahydroisoquinolin-8-ol (dl-corpaverine)

6,7-Dimethoxy-1-(4-0methoxybenzyl)-1,2,3,4-tetrahydroisoquinolin-8-ol (2.55 g, 7.74 mmol) obtained in Example 1–2 was dissolved in 100 ml of chloroform-methanol (1:1), 35% formalin (3.6 ml, 45.3 mmol) was added and the mixture was stirred at room temperature for 2hours. The solvent was removed under reduced pressure, 200 ml of water was added to the resultant residue, and the mixture was neutralized with 1 N hydrochloric acid and then extracted with chloroform (100 ml ×3). The organic layer was dried over anhydrous magnesium was purified by silica gel column chromatography (chloroform/methanol) to give 2.09 g (yield: 79%) of the captioned compound as pale yellow powder.

Melting: 112°–114° C.

FAB-MS (m/z, $(C_{20}H_{25}NO_4+H)^+$): 344

$^1$H-NMR (300 MHz, $CDCl_3$, δ ppm): 2.35 (3H, s), 2.35–2.45 (1H, m), 2.73–2.87 (2H, m), 2.98 (1H, dd, J=3.2 Hz, 14.2 Hz), 3.20–3.32 (1H, m), 3.78 (3H, s), 3.88 (3H), s), 3.95 (1H, d, J=3.2 Hz, 8.8 Hz), 6.20 (1H, s), 6.80 (1H, d, J= 8.8 Hz), 7.18 (1H, d, J=8.8 Hz)

As apparent from the foregoing, it is possible, according to the process of this invention, to obtain 6,7-dialkoxy-1,2,3,4-tetrahydroisoquinolin-8-ols, which have hitherto been difficult to synthesize, through 6,7-dialkoxy-3,4-dihydroisoquinolin-8-ols in a high yield.

What is claimed is:

1. A compound represented by the following formula or a salt thereof;

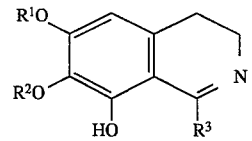

[I]

wherein $R^1$ and $R^2$ are independently a lower alkyl or benzyl group, or are combined together to form a methylene group; and $R^3$ is a hydrogen atom or a lower alkyl group, a benzyl group wherein 1 to 3 optional hydrogen atom(s) on the benzene ring may be replaced by an substituent(s) selected from the group consisting of a lower alkoxy group, a benzyloxy group, a halogen atom, a nitro group and a lower alkoxycarbonylmethyl group, a phenethyl group wherein 1 to 3 optional hydrogen atom(s) on the benzene ring may be replaced by a lower alkoxy or benzyloxy group, or a heteroarylmethyl or heteroarylethyl group, provided that when $R^3$ is a methyl group, $R^1$ and $R^2$ are not simultaneously methyl groups.

* * * * *